US007070629B2

(12) United States Patent
Kravtchenko et al.

(10) Patent No.: US 7,070,629 B2
(45) Date of Patent: Jul. 4, 2006

(54) DYE COMPOSITION COMPRISING AT LEAST ONE DIAMINOPYRAZOLE OXIDATION BASE, AT LEAST ONE PARAPHENYLENEDIAMINE OXIDATION BASE COMPRISING A CYCLIC AMINO GROUP, AND AT LEAST ONE COUPLER

(75) Inventors: Sylvain Kravtchenko, Asnieres (FR); Alain Lagrange, Coupvray (FR)

(73) Assignee: L'Oreal, S.A., Paris (FR)

( * ) Notice: Subject to any disclaimer, the term of this patent is extended or adjusted under 35 U.S.C. 154(b) by 201 days.

(21) Appl. No.: 10/491,217

(22) PCT Filed: Sep. 27, 2002

(86) PCT No.: PCT/FR02/03318

§ 371 (c)(1),
(2), (4) Date: Mar. 26, 2004

(87) PCT Pub. No.: WO03/028689

PCT Pub. Date: Apr. 10, 2003

(65) Prior Publication Data

US 2004/0231066 A1 Nov. 25, 2004

(30) Foreign Application Priority Data

Sep. 28, 2001 (FR) .......................................... 01 12529

(51) Int. Cl.
*A61K 7/13* (2006.01)

(52) U.S. Cl. ...................... 8/405; 8/406; 8/407; 8/408; 8/410; 8/421; 8/423; 8/570; 8/573; 8/690; 8/692; 548/372.5; 548/373.1

(58) Field of Classification Search ................... 8/405, 8/406, 407, 408, 410, 421, 423, 570, 573, 8/690, 692; 548/372.5, 373.1
See application file for complete search history.

(56) References Cited

U.S. PATENT DOCUMENTS

| 4,003,699 | A | | 1/1977 | Rose et al. ................... 8/10.2 |
|---|---|---|---|---|
| 4,823,985 | A | | 4/1989 | Grollier et al. ................ 222/1 |
| 5,061,289 | A | | 10/1991 | Clausen et al. ................ 8/405 |
| 5,380,340 | A | | 1/1995 | Neunhoeffer et al. .......... 8/409 |
| 5,534,267 | A | * | 7/1996 | Neunhoeffer et al. ....... 424/701 |
| 5,663,366 | A | * | 9/1997 | Neunhoeffer et al. .... 548/371.4 |
| 5,718,731 | A | * | 2/1998 | Loewe et al. .................. 8/409 |
| 5,766,576 | A | | 6/1998 | Lowe et al. ................... 424/62 |
| 5,851,237 | A | | 12/1998 | Anderson et al. ............. 8/409 |
| 5,876,464 | A | | 3/1999 | Lim et al. ...................... 8/409 |
| 5,993,491 | A | | 11/1999 | Lim et al. ...................... 8/409 |
| 6,099,592 | A | | 8/2000 | Vidal et al. .................... 8/409 |
| 6,099,593 | A | | 8/2000 | Terranova et al. ............. 8/409 |
| 6,284,003 | B1 | | 9/2001 | Rose et al. .................... 8/412 |
| 6,338,741 | B1 | | 1/2002 | Burande et al. ............... 8/409 |
| 6,436,152 | B1 | | 8/2002 | Wella et al. ................... 8/405 |
| 6,503,282 | B1 | | 1/2003 | Braun ........................... 8/409 |
| 6,554,871 | B1 | | 4/2003 | Wella ........................... 8/409 |
| 6,613,313 | B1 | | 9/2003 | Kimura ..................... 474/70.1 |
| 6,645,258 | B1 | | 11/2003 | Burande et al. ............... 8/405 |
| 6,730,789 | B1 | | 5/2004 | Birault et al. ................ 546/121 |
| 6,800,097 | B1 | | 10/2004 | Wella et al. ................... 8/405 |
| 2001/0009044 | A1 | | 7/2001 | Braun ........................... 8/405 |
| 2002/0197223 | A1 | | 12/2002 | Kimura .................... 424/70.1 |
| 2003/0093866 | A1 | | 5/2003 | Vidal et al. .................... 8/405 |
| 2004/0074013 | A1 | | 4/2004 | Terranova et al. ............. 8/405 |

FOREIGN PATENT DOCUMENTS

| DE | 2 359 399 | | 6/1975 |
|---|---|---|---|
| DE | 38 43 892 | A1 | 6/1990 |
| DE | 4 133 957 | A1 | 4/1993 |
| DE | 42 34 885 | A1 | 4/1994 |
| DE | 4 241 532 | A1 | 6/1994 |
| DE | 195 43 988 | A1 | 5/1997 |
| DE | 196 43 059 | A | 4/1998 |
| DE | 196 46 609 | A1 | 5/1998 |
| EP | 0 692 245 | B1 | 1/1996 |
| EP | 0 770 375 | B1 | 11/1997 |
| EP | 0 891 765 | B1 | 1/1999 |
| EP | 0 962 451 | A2 | 12/1999 |
| EP | 1 116 711 | A2 | 7/2000 |
| FR | 2 586 913 | A1 | 3/1987 |
| FR | A-2 733 749 | A1 | 11/1996 |
| FR | A-2 750 048 | A1 | 12/1997 |
| FR | 2 801 308 | A1 | 5/2001 |
| FR | 2 806 299 | A1 | 9/2001 |
| FR | 2 817 471 | A1 | 6/2002 |
| GB | 1 026 978 | | 4/1966 |
| GB | 1 153 196 | | 5/1969 |
| JP | 63-169 571 | A | 7/1988 |
| JP | 05 163 124 | A | 6/1993 |
| JP | 11 158 048 | A | 12/1997 |
| WO | WO 94/08969 | A1 | 4/1994 |
| WO | WO 94/08970 | A1 | 4/1994 |
| WO | WO 96/15764 | A1 | 5/1996 |
| WO | WO 01 51019 | A1 | 7/2001 |

OTHER PUBLICATIONS

Juffermans, J.H.P.; Habraken, C.L.; Selective Thermolysis Reactions of Bromo–1–nitro–1H–pyrazoles. Formation of 3–Nitro–1H–vs. 4–Nitro–1H–pyrazoles,; J. Org. Chem. 1986, 51, 4656.
Klebe et al.; "A Facile Synthesis of 3(5)–Aminopyrazoles"; Synthesis, 1973, 294.
International Search Report, dated Feb. 3, 2003.
English language Derwent Abstract of DE 196 46 609 A1, dated May 14, 1998.

(Continued)

*Primary Examiner*—Mark Kopec
*Assistant Examiner*—Eisa Elhilo
(74) *Attorney, Agent, or Firm*—Finnegan, Henderson, Farabow, Garrett & Dunner, LLP

(57) ABSTRACT

The invention relates to a dye composition comprising a first oxidation base of the diaminopyrazole type, a second oxidation base of the para-phenylenediamine type containing a cyclic amino group, and a coupler.

The invention also relates to the use of this composition for dyeing keratin fibers and also to the dyeing process using this composition.

28 Claims, No Drawings

OTHER PUBLICATIONS

English language Derwent Abstract of EP 0 770 375 B1, dated Sep. 13, 1996.
English language Derwent Abstract of DE 4 241 532 A1, dated Jun. 16, 1994.
English language Derwent Abstract of EP 0 770 375 B1, dated Sep. 13, 1996.
English language Derwent Abstract of 05 163 124 A, dated Jun. 29, 1993.
English language Derwent Abstract of JP 63–169 571, dated Jul. 7, 1988.
Huttel, R.; Buchele, F.; "Uber N–Nitro–pyrazole"; Chem. Ber.; 1955, 88, 1586.

* cited by examiner

DYE COMPOSITION COMPRISING AT LEAST ONE DIAMINOPYRAZOLE OXIDATION BASE, AT LEAST ONE PARAPHENYLENEDIAMINE OXIDATION BASE COMPRISING A CYCLIC AMINO GROUP, AND AT LEAST ONE COUPLER

The invention relates to a dye composition comprising a first oxidation base of the diaminopyrazole type, a second oxidation base of the para-phenylenediamine type containing a cyclic amino group, and a coupler. The invention also relates to the use of this composition for dyeing keratin fibres and also to the dyeing process using this composition.

It is known practice to dye keratin fibres and in particular human hair with dye compositions containing oxidation dye precursors, generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes must moreover satisfy a certain number of requirements. Thus, it must have no toxicological drawbacks, it must allow shades to be obtained in the desired intensity, and it must show good resistance to external agents such as light, bad weather, washing, permanent waving, perspiration and rubbing.

The dyes must also make it possible to cover white hair and, finally, they must be as unselective as possible, i.e. they must produce the smallest possible colour differences along the same length of keratin fibre, which is generally differently sensitized (i.e. damaged) between its end and its root.

Dye compositions comprising diaminopyrazole derivatives as oxidation bases are already known. For example, patent application DE 3 843 892 describes dye compositions for dyeing keratin fibres, comprising 4,5-diaminopyrazole derivatives that may be substituted in position 2 with alkyl or hydroxyalkyl radicals. Patent application EP 692 245 describes dye compositions comprising 4,5-diaminopyrazole derivatives combined with particular meta-phenylenediamines. Patent application DE 196 43 059 describes dye compositions combining 4,5-diaminopyrazole derivatives with meta-aminophenol and meta-phenylenediamine couplers. Patent application DE 196 46 609 describes dye compositions combining 4,5-diaminopyrazole derivatives with benzoxazine couplers.

Furthermore, it is known practice from patent application JP 11 158 048 to use dye compositions comprising para-phenylenediamine derivatives, one of the nitrogen atoms of which is in a 5- to 7-membered ring. U.S. Pat. No. 5,851,237 proposes the use of 1-(4-aminophenyl)pyrrolidine derivatives optionally substituted on the benzene nucleus, to replace para-phenylenediamine. U.S. Pat. No. 5,993,491 proposes the use of N-(4-aminophenyl)-2-(hydroxymethyl) pyrrolidine derivatives optionally substituted on the benzene nucleus, to replace para-phenylenediamine.

However, the shades obtained using dye compositions containing this type of oxidation base are not sufficiently strong, chromatic and/or fast.

The aim of the present invention is to provide novel dye compositions for dyeing keratin fibres, containing diaminopyrazole derivatives, which do not have the drawbacks of those of the prior art. In particular, the aim of the present invention is to provide dye compositions containing diaminopyrazole derivatives that are relatively unselective and particularly fast, while at the same time being capable of generating intense colorations in varied shades.

This aim is achieved with the present invention, one subject of which is a dye composition comprising, in a suitable dyeing medium:

at least one 4,5-diaminopyrazole oxidation base of formula (I) or the corresponding addition salts

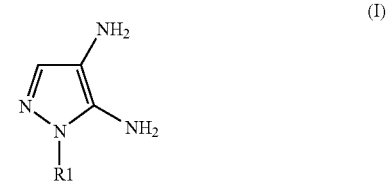

(I)

in which R1 is a $C_1$–$C_6$ alkyl radical substituted with one or more radicals OR, R being a $C_1$–$C_6$ alkyl radical;

at least one oxidation base chosen from the para-phenylenediamine derivatives of formula (II) below, or the addition salts thereof

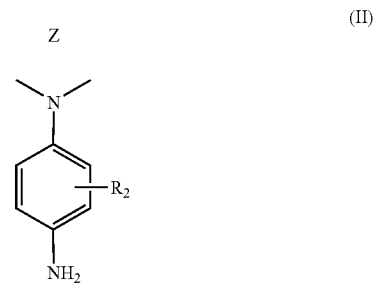

(II)

in which

Z represents the atoms required to form a 3- to 8-membered saturated ring, these atoms possibly being carbon or nitrogen atoms and preferably only carbon atoms, the ring possibly being substituted, $R_2$ represents a hydrogen atom; a halogen atom chosen from a chlorine atom and a bromine atom; a linear or branched, saturated or unsaturated $C_1$–$C_7$ hydrocarbon-based chain, one or more carbon atoms of which may be replaced with an oxygen, nitrogen or sulphur atom or with an $SO_2$ group, and the carbon atoms of which may be, independently of each other, substituted with one or more halogen atoms; the said radical $R_2$ not comprising a peroxide bond or diazo, nitro or nitroso radicals, at least one coupler.

The composition of the present invention makes it possible in particular to obtain a chromatic, very strong, relatively unselective, and fast coloration of keratin fibres.

Another subject of the invention is the use of the composition of the present invention for dyeing keratin fibres, in particular human keratin fibres such as the hair.

A subject of the invention is also a dyeing device and a dyeing process using the composition of the invention.

In the context of the present invention, the term "alkyl" means linear or branched radicals comprising, unless otherwise indicated, from 1 to 10 carbon atoms and preferably 1 to 6 carbon atoms, for example methyl, ethyl, n-propyl, isopropyl, butyl, etc. The term "alkoxy" means alkyl-O—, the alkyl radical being as defined above.

According to one particular embodiment, the 4,5-diaminopyrazole oxidation base of formula (I) is such that R1 represents a $C_1$–$C_4$ and preferably C2–C4 alkyl radical substituted with a radical OR, R being a $C_1$–$C_4$ and preferably C1–C2 alkyl radical. Preferably, the oxidation base of formula (I) is 4,5-diamino-1-(2'-methoxyethyl)pyrazole.

According to the present invention, the ring formed with Z and the nitrogen atom of the para-phenylenediamine may be a pyrrolidine, piperidine, homopiperidine, imidazoline, pyrazolidine or piperazine ring. The saturated ring thus formed may be substituted. Examples of substituents that may be mentioned include halogen atoms, a hydroxyl radical, an amino radical, $C_1$–$C_4$ alkyl radicals, optionally substituted with one or more hydroxyl, amino, $C_1$–$C_2$ (di) alkylamino or carboxyl radicals; a carboxyl radical; carbamoyl or sulphonamide radicals; radicals —OR5 in which R5 represents a C1–C4 alkyl radical substituted with one or more radicals chosen from a halogen atom, C1–C2 alkoxy radicals, amino radicals, C1–C2 aminoalkyl radicals or C3–C4 alkyl radicals substituted with one or more hydroxyl radicals; a methylcarbonyl radical; a radical —NR6R7 in which R6 and R7 represent, independently of each other, a hydrogen atom, a C1–C4 alkyl radical substituted with one or more radicals chosen from a halogen atom, hydroxyl radicals, C1–C2 alkoxy radicals, amino radicals or C1–C2 aminoalkyl radicals.

According to one particular embodiment, Z represents the carbon atoms required to form a 5- to 8-membered ring, preferably a substituted or unsubstituted pyrrolidine ring.

According to the invention, a linear or branched, saturated or unsaturated hydrocarbon-based chain of formula (II) is a chain that may comprise one or more double bonds and/or one or more triple bonds, and which can form one or more 3- to 6-membered rings, the double bonds optionally being able to lead to aromatic groups. When it is indicated that one or more of the carbon atoms of R2 may be replaced with an oxygen, nitrogen or sulphur atom or with an $SO_2$ group, and/or when the said radical R2 may be unsaturated, this means that the following conversions may be performed, for example:

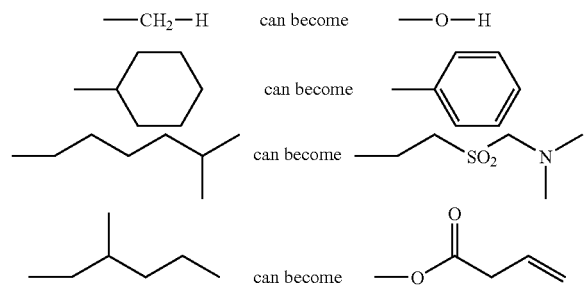

According to the invention, R2 preferably represents a hydrogen atom, an alkyl radical, an alkenyl radical, an alkynyl radical, an alkoxyalkyl radical, a hydroxyalkyl radical, an alkoxy radical, an allyloxy radical, a hydroxyaminoalkyl radical, a hydroxyalkoxy radical, a carboxyalkyl radical or an aminoalkyl radical.

By way of example, mention may be made, for R2, of methyl, ethyl, isopropyl, vinyl, allyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, methoxy, ethoxy, allyloxy or 2-hydroxyethyloxy radicals. Preferably, R2 represents a hydrogen atom or a methyl, hydroxymethyl, 2-hydroxyethyl, 1,2-dihydroxyethyl, methoxy or 2-hydroxyethoxy radical, preferentially a hydrogen atom or a methyl radical.

According to one particular embodiment, the oxidation base chosen from para-phenylenediamine derivatives is a para-phenylenediamine derivative containing a pyrrolidine group, corresponding to formula (IIa) below

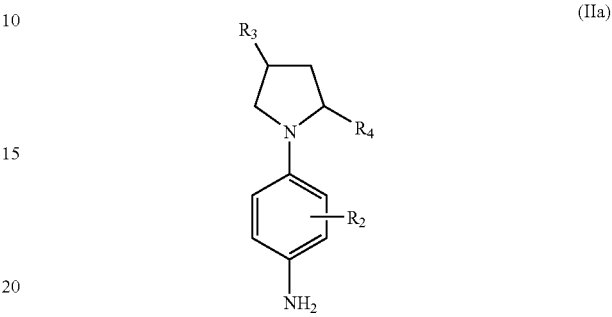

(IIa)

in which
R2 is as defined above,
R3 represents a hydrogen atom; a hydroxyl radical; an amino radical; a radical —OR5 in which R5 represents a C1–C4 alkyl radical substituted with one or more radicals chosen from a halogen atom and C1–C2 alkoxy, amino, C1–C2 aminoalkyl or C1–C4 monohydroxyalkyl or polyhydroxyalkyl radicals; a methylcarbonyl radical; a radical —NR6R7 in which R6 and R7 represent, independently of each other, a hydrogen atom or a C1–C4 alkyl radical which may be substituted with one or more radicals chosen from a halogen atom and hydroxyl, C1–C2 alkoxy, amino or C1–C2 aminoalkyl radicals,
R4 represents a hydrogen atom; a carbamoyl radical, an amido radical; a C1–C5 monohydroxyalkyl or polyhydroxyalkyl radical.

According to one particular embodiment, R3 represents a hydrogen atom or a hydroxyl, acetoxy, amino, alkylamino or hydroxyalkylamino radical. Examples that may be mentioned for R3 include a hydrogen atom and a hydroxyl, acetoxy, amino, methylamino, dimethylamino or 2-hydroxyethylamino radical. Preferably, R3 represents a hydrogen atom, a hydroxyl radical or an amino radical.

In formula (IIa), R4 preferably represents a hydrogen atom, a carbamoyl radical, a hydroxyl radical, a C1–C4 hydroxyalkyl radical or a methyl radical.

By way of example, the para-phenylenediamine derivatives of formula (II) are chosen from N-(4-aminophenyl)-3-hydroxypyrrolidine, N-(4-amino-2-methylphenyl)-3-hydroxypyrrolidine, N-(4-amino-2-ethylphenyl)-3-hydroxypyrrolidine, N-(4-amino-2-methoxyphenyl)-3-hydroxypyrrolidine, N-(4-amino-2-(2-hydroxyethyl)phenyl)-3-hydroxypyrrolidine, N-(4-amino-2-(1-hydroxyethyl)phenyl)-3-hydroxypyrrolidine, N-(4-amino-2-(1,2-dihydroxyethyl)phenyl)-3-hydroxypyrrolidine, N-(4-amino-3-methylphenyl)-3-hydroxypyrrolidine, N-(4-amino-3-ethylphenyl)-3-hydroxypyrrolidine, N-(4-amino-3-methoxyphenyl)-3-hydroxypyrrolidine, N-(4-amino-3-(2-hydroxyethyl)phenyl)-3-hydroxypyrrolidine, N-(4-amino-3-(1-hydroxyethyl)phenyl)-3-hydroxypyrrolidine, N-(4-amino-3-(1,2-dihydroxyethyl)phenyl)-3-hydroxypyrrolidine, N-(4-aminophenyl)-3-aminopyrrolidine, N-(4-amino-2-methylphenyl)-3-aminopyrrolidine, N-(4-amino-2-ethylphenyl)-3-aminopyrrolidine, N-(4-amino-2-methoxyphenyl)-3- aminopyrrolidine, N-(4-amino-2-(2-hydroxyethyl)phenyl)-3-aminopyrrolidine, N-(4-amino-2-(1-hydroxyethyl)phenyl)-3-aminopyrrolidine, N-(4-amino-2-(1,2-dihydroxyethyl)-phenyl)-3-hydroxypyrrolidine, N-(4-amino-3-methylphenyl)-3-aminopyrrolidine, N-(4-amino-3-ethylphenyl)-3-aminopyrrolidine, N-(4-amino-3-methoxyphenyl)-3-aminopyrrolidine, N-(4-amino-3-(2-hydroxyethyl)phenyl)-3-aminopyrrolidine, N-(4-amino-3-(1-hydroxyethyl)phenyl)-3-aminopyrrolidine, N-(4-amino-3-(1,2-dihydroxyethyl)phenyl)-3-aminopyrrolidine, 1-(4-aminophenyl)pyrrolidine, 1-(4-aminophenyl)-2-pyrrolidinemethanol, 1-(4-aminophenyl)-4-hydroxy-2-pyrrolidinemethanol and N-(4-aminophenyl)prolineamide, and the addition salts thereof with an acid. Preferably, the para-phenylenediamine derivatives of formula (IIa) are chosen from 3-hydroxy-1-(4'-aminophenyl)pyrrolidine, 3-amino-1-(4'-aminophenyl)pyrrolidine, 1-(4-aminophenyl)pyrrolidine, 1-(4-aminophenyl)-2-pyrrolidinemethanol, 1-(4-aminophenyl)-4-hydroxy-2-pyrrolidinemethanol and N-(4-aminophenyl)prolineamide, and the addition salts thereof.

The coupler that is useful in the composition of the present invention may be any coupler conventionally used in the field of dyeing. This coupler may be chosen from meta-phenylenediamines, meta-aminophenols, meta-diphenols, naphthalene-based couplers and heterocyclic couplers, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis-(β-hydroxyethylamino)toluene, and the addition salts thereof with an acid.

In the composition of the present invention, the coupler(s) is(are) each generally present in an amount of between 0.001% and 10% by weight approximately and preferably between 0.005% and 6% by weight relative to the total weight of the dye composition.

The composition of the present invention may also comprise one or more additional oxidation bases conventionally used in oxidation dyeing, other than those described above. By way of example, these additional oxidation bases are chosen from para-phenylenediamines other than those described above, bis(phenyl)alkylenediamines, para-aminophenols, ortho-aminophenols and heterocyclic bases other than those described above, and the addition salts thereof.

Among the para-phenylenediamines which can be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-thienyl-para-phenylenediamine, 2-β-hydroxyethylamino-5-aminotoluene and the addition salts thereof with an acid.

Among the para-phenylenediamines mentioned above that are particularly preferred are para-phenylenediamine, para-tolylenediamine, 2-isopropyl-para-phenylenediamine, 2-β-hydroxyethyl-para-phenylene-diamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid are more particularly preferred.

Among the bis(phenyl)alkylenediamines which can be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)-ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols which can be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned, for example, are 2-aminophenol, 2-amino-5-methylphenol, 2-amino-6-methylphenol and 5-acetamido-2-aminophenol, and the addition salts thereof with an acid.

Among the heterocyclic bases other than those useful in the present invention mention may be made, for example, of pyridine derivatives, pyrimidine derivatives and pyrazole derivatives other than those of the invention.

Among the pyridine derivatives which may be mentioned are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid or a base.

Other pyridine oxidation bases that are useful in the present invention are the 3-amino-pyrazolo[1,5-a]pyridine oxidation bases or the addition salts thereof described, for example, in patent application FR 2 801 308. By way of example, mention may be made of pyrazolo[1,5-a]pyrid-3- ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]-ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol and also the addition salts thereof with an acid or with a base.

Among the pyrimidine derivatives which may be mentioned are the compounds described, for example, in German patent DE 2 359 399 or Japanese patents JP 88-169 571; JP 05 163 124; EP 0 770 375 or patent application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo-[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]-pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid and the tautomeric forms thereof, when a tautomeric equilibrium exists.

Among the pyrazole derivatives which may be mentioned are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The oxidation base(s) present in the composition of the invention is (are) each generally present in an amount of between 0.001% and 10% by weight approximately relative to the total weight of the dye composition, and preferably between 0.005% and 6%.

In general, the addition salts of the oxidation bases and of the couplers that may be used in the context of the invention are chosen especially from the addition salts with an acid, such as the hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, ammonia, amines or alkanolamines.

The dye composition in accordance with the invention may also contain one or more direct dyes that may be chosen especially from nitrobenzene dyes, azo direct dyes and methine direct dyes. The direct dyes may be of nonionic, anionic or cationic nature.

The medium that is suitable for dyeing, also known as the dye support, generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The solvents are present in proportions preferably of between 1% and 40% by weight approximately relative to the total weight of the dye composition, and even more preferably between 5% and 30% by weight approximately.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, and in particular anionic, cationic, nonionic or amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

The above adjuvants are generally present in an amount for each of them of between 0.01% and 20% by weight relative to the weight of the composition.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The pH of the dye composition in accordance with the invention is generally between about 3 and 12 and preferably between about 5 and 11. It may be adjusted to the desired value using acidifying or basifying agents usually used in the dyeing of keratin fibres, or alternatively using standard buffer systems.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (III) below:

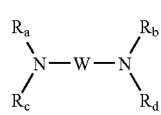

(III)

in which W is a propylene residue which is unsubstituted or substituted with a hydroxyl group or a $C_1$–$C_4$ alkyl radical; $R_a$, $R_b$, $R_c$ and $R_d$, which may be identical or different, represent a hydrogen atom, a $C_1$–$C_4$ alkyl radical or a $C_1$–$C_4$ hydroxyalkyl radical.

The dye composition according to the invention may be in various forms, such as in the form of liquids, creams or gels, or in any other form that is suitable for dyeing keratin fibres, and especially human hair.

According to the dyeing process of the present invention, the composition according to the present invention is applied to the fibres, and the colour is developed using an oxidizing agent. The colour may be developed at acidic, neutral or alkaline pH and the oxidizing agent may be mixed with the composition of the invention just at the time of use, or it may be used starting with an oxidizing composition containing it, which is applied simultaneously or sequentially to the composition of the invention.

According to one particular embodiment, the composition according to the present invention is mixed, preferably at the time of use, with a composition containing, in a medium that is suitable for dyeing, at least one oxidizing agent, this oxidizing agent being present in an amount that is sufficient to develop a coloration. The mixture obtained is then applied to the keratin fibres. After an action time of 3 to 50 minutes approximately, preferably 5 to 30 minutes approximately, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulphates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in compositions for dyeing the hair and as defined above for the composition of the invention.

The pH of the oxidizing composition containing the oxidizing agent is such that, after mixing with the dye composition, the pH of the resulting composition applied to the keratin fibres ranges between 3 and 12 approximately and preferably between 5 and 11. It may be adjusted to the desired value by means of acidifying or basifying agents usually used in the dyeing of keratin fibres and as defined above.

The ready-to-use composition that is finally applied to the keratin fibres may be in various forms, such as in the form of liquids, creams or gels or any other form that is suitable for dyeing keratin fibres, and especially human hair.

Another subject of the invention is a multi-compartment dyeing device or "kit", in which a first compartment contains the dye composition of the invention defined above and a second compartment contains an oxidizing composition. This device may be equipped with a means for applying the desired mixture to the hair, such as the devices described in patent FR-2 586 913 in the name of the Applicant.

The diaminopyrazole compounds that are useful in the composition of the present invention are known compounds that may be obtained using general preparation processes known to those skilled in the art. For example, the synthetic approach shown below is described in the literature up to the intermediate (2) (J. H. P. Juffermanns, C. L; Habraken; J. Org. Chem. 1986, 51, 4656; Klebe et al.; Synthesis, 1973, 294; R. Hüttel, F. Buchele; Chem. Ber.; 1955, 88, 1586). In the present case, the conversion of compound 3 into compound 2 is performed using an $NH_3$/EtOH mixture.

The alkylation and the amination to obtain the compounds of formula (1) according to the invention are mentioned in document DE 42 34 885.

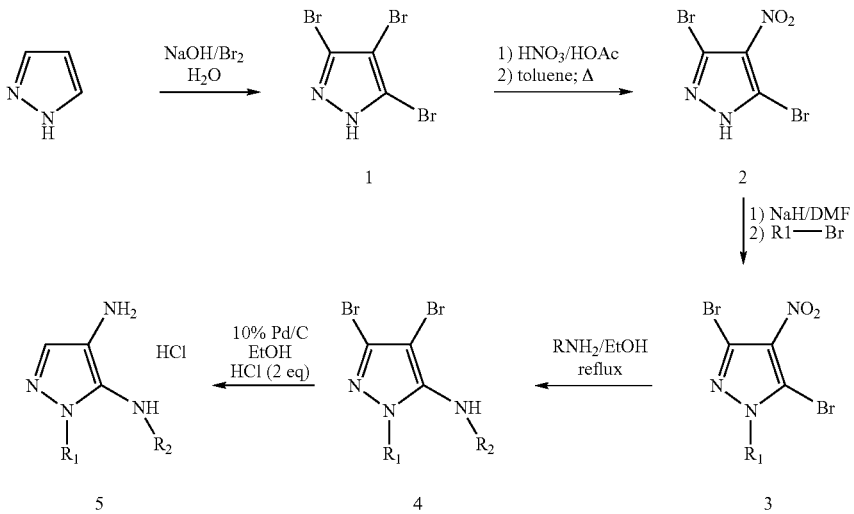

The para-phenylenediamine derivatives that are useful in the context of the present invention are known compounds that may be obtained using conventional syntheses within the scope of a person skilled in the art. In particular, the para-phenylenediamine derivatives containing a pyrrolidine group may be prepared according to the synthetic processes described especially in patent application DE 4 241 532 (AGFA), FR 2 806 299, U.S. Pat. No. 5,851,237, U.S. Pat. No. 5,876,464 and U.S. Pat. No. 5,993,491.

The examples that follow serve to illustrate the invention without, however, being limiting in nature.

EXAMPLES

Example 1

Synthesis of 4,5-diamino-1-(2'-methoxyethyl) pyrazole dihydrochloride

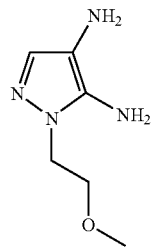

A mixture of 5-benzylamino-3-bromo-1-(2'-methoxyethyl)-4-nitropyrazole (4 g, 2.8 mmol) in ethanol (500 ml) containing a 10% Pd/C catalyst (Johnson-Mattey Type 487, dry weight 0.5 g) and 36% hydrochloric acid (0.57 g, 5.6 mmol) is hydrogenated in a Parr Autoclave (1 l) at 1 MPa for 1 hour. The catalyst is then removed by filtration and washed with ethanol, and the filtrate is evaporated under reduced pressure. A crude orange-coloured solid (2.8 g) is thus obtained, and is triturated in EtOAc (20 ml) for 1 hour. The solid is then filtered off and washed with cold EtOAc (20 ml) and then dried under vacuum to give the 4,5-diamino-1-(2'-methoxyethyl)pyrazole in the form of a beige-coloured solid (0.7 g, 27%).

HPLC (purity): 99.5%. m.p.: 168.1–173.0° C. $^1$H NMR: (400 MHz, d$^6$-DMSO): 7.34 (1H, s, NH$_{arom}$), 5.18 (1H, s$_{broad}$, NH), 4.09 (2H, t, J=5.5 Hz, CH$_2$N), 3.61 (2H, t, J=5.5 Hz, CH$_2$O), 3.23 (3H, s, OCH$_3$).

Example 2

Dye composition containing 4,5-diamino-1-(2'-methoxyethyl)pyrazole dihydrochloride The following dye composition was prepared:

| Example | 2 |
|---|---|
| 4,5-Diamino-1-(2'-methoxyethyl)-pyrazole 2HCl | 0.744 g |
| 1-(4-Aminophenyl)-3-hydroxypyrrolidine | 0.762 g |
| 1-Methyl-4-aminophenol | 0.78 g |
| Dye support | (*) |
| Demineralized water q.s. | 100 g |

Dye support

| | |
|---|---|
| Benzyl alcohol | 2 g |
| Polyethylene glycol 8 EO | 3 g |
| Ethanol | 18 g |
| (C8–C10)alkyl polyglucoside as an aqueous solution containing 60% active material buffered with ammonium citrate, sold under the name Oramix CG110 by SEPPIC | 5 g in this case |
| Ammonia at 20% NH$_3$ | 10 g |
| Sodium metabisulphite | 0.205 g |
| Sequestering agent | q.s. |

At the time of use, the composition is mixed with an equal weight of 20-volumes aqueous hydrogen peroxide solution (6% by weight).

The mixture obtained is applied to locks of natural and permanent-waved grey hair containing 90% white hairs, at a rate of 10 g per 1 g of hair. After an action time of 30 minutes, the locks are rinsed, washed with a standard shampoo, rinsed again and then dried.

The locks are assessed visually. An ashy dark-purple coloration is thus obtained.

What is claimed is:

1. A dye composition comprising, in a suitable dyeing medium,
   at least one first oxidation base chosen from 4,5-diaminopyrazole oxidation bases of formula (I) and addition salts thereof:

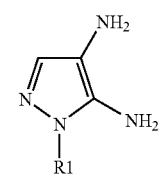

wherein R$_1$ is chosen from C$_1$–C$_6$ alkyl radicals substituted with least one radical OR, wherein R is chosen from C$_1$–C$_6$ alkyl radicals;
   at least one second oxidation base chosen from para-phenylenediamine derivatives of formula (II) and addition salts thereof:

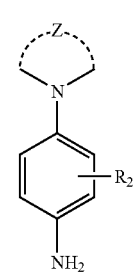

wherein:
   Z represents the atoms required to form a 3- to 8-membered saturated ring, wherein the atoms are optionally chosen from carbon and nitrogen atoms, and the ring may optionally be substituted;
   R$_2$ is chosen from hydrogen, chlorine, and bromine atoms; linear and branched, saturated and unsaturated C$_1$–C$_7$ hydrocarbon-based chains, wherein at least one of the carbon atoms may be replaced with at least one entity chosen from oxygen, nitrogen, and sulphur atoms and an SO$_2$ group, and wherein the carbon atoms may, independently of each other, be substituted with at least one halogen atom; provided that the radical R$_2$ does not comprise a peroxide bond, a diazo radical, a nitro radical, or a nitroso radical; and
   at least one coupler.

2. The composition according to claim 1, wherein, in formula (I), R$_1$ is chosen from C$_1$–C$_4$ alkyl radicals substituted with at least one radical OR, wherein R is chosen from C$_1$–C$_4$ alkyl radicals.

3. The composition according to claim 1, wherein the at least one first oxidation base is 4,5-diamino-1-(2'-methoxyethyl)pyrazole.

4. The composition according to claim 1 wherein, in formula (II), Z represents the carbon atoms required to form a saturated 5- to 8-membered ring.

5. The composition according to claim 1, wherein R$_2$ is chosen from a hydrogen atom, alkyl radicals, alkenyl radicals, alkynyl radicals, alkoxyalkyl radicals, hydroxyalkyl radicals, alkoxy radicals, allyloxy radicals, hydroxyaminoalkyl radicals, hydroxyalkoxy radicals, carboxyalkyl radicals, and aminoalkyl radicals.

6. The composition according to claim 5, wherein $R_2$ is chosen from a hydrogen atom and methyl, ethyl, isopropyl, vinyl, allyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, methoxy, ethoxy, allyloxy, and 2-hydroxyethyloxy radicals.

7. The composition according to claim 6, wherein $R_2$ is chosen from a hydrogen atom and methyl, hydroxymethyl, 2-hydroxyethyl, 1,2-dihydroxyethyl, methoxy, and 2-hydroxyethoxy radicals.

8. The composition according to claim 1, wherein Z represents only carbon atoms.

9. The composition according to claim 1, wherein the at least one second oxidation base is chosen from para-phenylenediamine derivatives of formula (IIa) below and addition salts thereof:

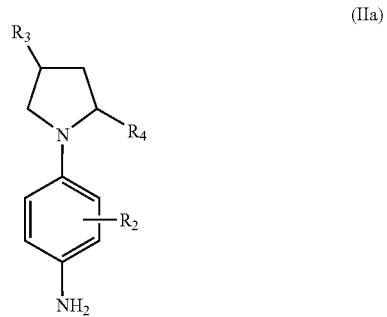

(IIa)

wherein:
- $R_2$ is chosen from hydrogen, chlorine, and bromine atoms; linear and branched, saturated and unsaturated $C_1-C_7$ hydrocarbon-based chains, wherein at least one of the carbon atoms may be replaced with at least one entity chosen from oxygen, nitrogen and sulphur atoms and an $SO_2$ group, and wherein the carbon atoms may, independently of each other, be substituted with at least one halogen atom; provided that the radical $R_2$ does not comprise a peroxide bond, a diazo radical, a nitro radical, or a nitroso radical;
- $R_3$ is chosen from a hydrogen atom, a hydroxyl radical; an amino radical; a radical —$OR_5$ wherein $R_5$ is chosen from $C_1-C_4$ alkyl radicals substituted with at least one radical chosen from a halogen atom and $C_1-C_2$ alkoxy, amino, $C_1-C_2$ aminoalkyl, $C_1-C_4$ monohydroxyalkyl, and polyhydroxyalkyl radicals; a methylcarbonyl radical; a radical —$NR_6R_7$ wherein $R_6$ and $R_7$, which may be identical or different, are each chosen from a hydrogen atom and $C_1-C_4$ alkyl radicals which may be substituted with at least one radical chosen from a halogen atom and hydroxyl, $C_1-C_2$ alkoxy, amino and $C_1-C_2$ aminoalkyl radicals; and
- $R_4$ is chosen from a hydrogen atom; a carbamoyl radical, an amido radical, and $C_1-C_5$ monohydroxyalkyl and polyhydroxyalkyl radicals.

10. The composition according to claim 9, wherein $R_3$ is chosen from a hydrogen atom and hydroxyl, acetoxy, amino, alkylamino, and hydroxyalkylamino radicals.

11. The composition according to claim 10, wherein $R_3$ is chosen from a hydrogen atom and hydroxyl, acetoxy, amino, methylamino, dimethylamino, and 2-hydroxyathylamino radicals.

12. The composition according to claim 11, wherein $R_3$ is chosen from a hydrogen atom, a hydroxyl radical, and an amino radical.

13. The composition according to claim 9, wherein $R_4$ is chosen from a hydrogen atom, a carbamoyl radical, $C_1-C_4$ hydroxyalkyl radicals, and a methyl radical.

14. The composition to claim 1, wherein the para-phenylenediamine derivatives of formula (II) are chosen from N-(4-aminophenyl)-3-hydroxypyrrolidine, N-(4-amino-2-methylphenyl )-3-hydroxypyrrolidine, N-(4-amino-2-ethylphenyl)-3-hydroxypyrrolidine, N-(4-amino-2-methoxyphenyl)-3-hydroxypyrrolidine, N-(4-amino-2-(2-hydroxyethyl)phenyl)-3-hydroxypyrrolidine, N-(4-amino-2-(1-hydroxyethyl)phenyl)-3-hydroxypyrrolidine, N-(4-amino-2-(1,2-dihydroxyethyl)phenyl )-3-hydroxypyrrolidine, N-(4-amino-3-methylphenyl)-3-hydroxypyrrolidine, N-(4-amino-3-ethylphenyl)-3-hydroxypyrrolidine, N-(4-amino-3-methoxyphenyl)-3-hydroxypyrrolidine, N-(4-amino-3-(2-hydroxyethyl )phenyl)-3-hydroxypyrrolidine, N-(4-amino-3-(1-hydroxyethyl)phenyl)-3-hydroxypyrrolidine, N-(4-amino-3-(1,2-dihydroxyethyl)phenyl)-3-hydroxypyrrolidine, N-(4-aminophenyl)-3-aminopyrrolidine, N-(4-amino-2-methylphenyl)-3-aminopyrrolidine, N-(4-amino-2-ethylphenyl)-3-aminopyrrolidine, N-(4-amino-2-methoxyphenyl)-3-aminopyrrolidine, N-(4-amino-2-(2-hydroxyethyl)phenyl)-3-aminopyrrolidine, N-(4-amino-2-(-hydroxyethyl)phenyl)-3-aminopyrrolidine, N-(4-amino-2-(1,2-dihydroxyethyl)-phenyl)-3-hydroxypyrrolidine, N-(4-amino-3-methylphenyl)-3-aminopyrrolidine, N-(4-amino-3-ethylphenyl )-3-aminopyrrolidine, N-(4-amino-3-methoxyphenyl)-3-aminopyrrolidine, N-(4-amino-3-(2-hydroxyethyl)phenyl)-3-aminopyrrolidine, N-(4-amino-3-(1-hydroxyethyl)phenyl)-3-aminopyrrolidine, N-(4-amino-3-(1,2-dihydroxyethyl)phenyl)-3-aminopyrrolidine, 1-(4-aminophenyl)pyrrolidine, 1-(4-aminophenyl)-2-pyrrolidinemethanol, 1-(4-aminophenyl)-4-hydroxy-2-pyrrolidinemethanol, N-(4-aminophenyl)prolineamide, and acid addition salts thereof.

15. The composition according to claim 1, wherein the at least one coupler is chosen from meta-phenylenediamines, meta-aminophenols, meta-diphenols, naphthalenic couplers, heterocyclic couplers, and addition salts thereof.

16. The composition according to claim 15, wherein the at least one coupler is present in an amount ranging from 0.001 to 10% by weight, relative to the total weight of the dye composition.

17. The composition according to claim 1, further comprising at least one additional oxidation base chosen from para-phenylenediamines other than the oxidation bases of formula (II) and (IIa), bis(phenyl)alkylenediamines, para-aminophenols, ortho-aminophenols and heterocyclic bases, other than the oxidation bases of formula (I), and addition salts thereof.

18. The composition according to claim 1, wherein the at least one first oxidation base and the at least one second oxidation base are each present in an amount ranging from 0.001% to 10% by weight, relative to the total weight of the dye composition.

19. The composition according to claim 18, wherein the at least one first oxidation base and the at least one second oxidation base are each present in an amount ranging from 0.005% to 6% by weight, relative to the total weight of the dye composition.

20. The composition according to claim 1, further comprising at least one oxidizing agent.

21. The composition according to claim 20, wherein the at least one oxidizing agent is chosen from hydrogen peroxide, urea peroxide, alkali metal bromates, persalts, peracids, and oxidase enzymes.

22. The composition according to claim 1, further comprising at least one direct dye.

23. A process for the oxidation dyeing of keratin fibers, comprising,
applying to the fibers at least one dye composition comprising,
at least one first oxidation base chosen from 4,5-diaminopyrazole oxidation bases of formula (I) and addition salts thereof:

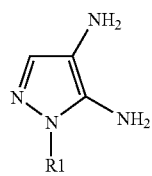

(I)

wherein $R_1$ is chosen from $C_1$–$C_6$ alkyl radicals substituted with least one radical OR, wherein R is chosen from $C_1$–$C_6$ alkyl radicals;
at least one second oxidation base chosen from para-phenylenediamine derivatives of formula (II) and addition salts thereof:

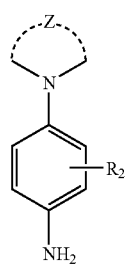

(II)

wherein:
Z represents the atoms required to form a 3- to 8-membered saturated ring, wherein the atoms are optionally chosen from carbon and nitrogen atoms, and the ring may optionally be substituted;
$R_2$ is chosen from hydrogen, chlorine, and bromine atoms; linear and branched, saturated and unsaturated $C_1$–$C_7$ hydrocarbon-based chains, wherein at least one of the carbon atoms may be replaced with at least one entity chosen from oxygen, nitrogen, and sulphur atoms and an $SO_2$ group, and wherein the carbon atoms may, independently of each other, be substituted with at least one halogen atom; provided that the radical $R_2$ does not comprise a peroxide bond, a diazo radical, a nitro radical, or a nitroso radical; and
at least one coupler and
developing a color with at least one oxidizing agent.

24. The process according to claim 23, wherein the at least one oxidizing agent is chosen from hydrogen peroxide, urea peroxide, alkali metal bromates, persalts, peracids, and oxidase enzymes.

25. The process according to claim 23, wherein the at least one oxidizing agent is mixed at the time of application with the at least one dye composition.

26. The process according to claim 23, wherein the at least one oxidizing agent is applied to the fibers in the form of an oxidizing composition, simultaneously with or sequentially to the at least one dye composition.

27. A multi-compartment device comprising,
at least one first compartment comprising at least one dyeing composition comprising,
at least one first oxidation base chosen from 4,5-diaminopyrazole oxidation bases of formula (I) and addition salts thereof:

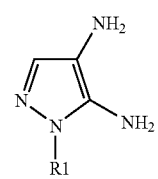

(I)

wherein $R_1$ is chosen from $C_1$–$C_6$ alkyl radicals substituted with least one radical OR, wherein R is chosen from $C_1$–$C_6$ alkyl radicals;
at least one second oxidation base chosen from para-phenylenediamine derivatives of formula (II) and addition salts thereof:

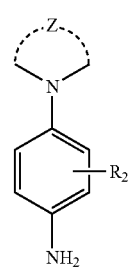

(II)

wherein:
Z represents the atoms required to form a 3- to 8-membered saturated ring, wherein the atoms are optionally chosen from carbon and nitrogen atoms, and the ring may optionally be substituted;
$R_2$ is chosen from hydrogen, chlorine, and bromine atoms; linear and branched, saturated and unsaturated $C_1$–$C_7$ hydrocarbon-based chains, wherein at least one of the carbon atoms may be replaced with at least one entity chosen from oxygen, nitrogen, and sulphur atoms and an $SO_2$ group, and wherein the carbon atoms may, independently of each other, be substituted with at least one halogen atom; provided that the radical $R_2$ does not comprise a peroxide bond, a diazo radical, a nitro radical, or a nitroso radical; and
at least one coupler and
at least one second compartment comprising at least one oxidizing composition.

28. A method for dyeing keratin fibers comprising applying, at least one dye composition, in a medium appropriate for dyeing, comprising,
at least one first oxidation base chosen from 4,5-diaminopyrazole oxidation bases of formula (I) and addition salts thereof:

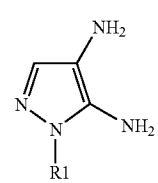

(I)

wherein $R_1$ is chosen from $C_1$–$C_6$ alkyl radicals substituted with least one radical OR, wherein R is chosen from $C_1$–$C_6$ alkyl radicals;
at least one second oxidation base chosen from para-phenylenediamine derivatives of formula (II) and addition salts thereof:

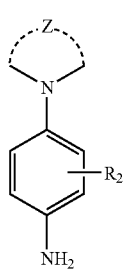

(II)

wherein:

Z represents the atoms required to form a 3- to 8-membered saturated ring, wherein the atoms are optionally chosen from carbon and nitrogen atoms, and the ring may optionally be substituted;

$R_2$ is chosen from hydrogen, chlorine, and bromine atoms; linear and branched, saturated and unsaturated $C_1$–$C_7$ hydrocarbon-based chains, wherein at least one of the carbon atoms may be replaced with at least one entity chosen from oxygen, nitrogen, and sulphur atoms and an $SO_2$ group, and wherein the carbon atoms may, independently of each other, be substituted with at least one halogen atom; provided that the radical $R_2$ does not comprise a peroxide bond, a diazo radical, a nitro radical, or a nitroso radical; and at least one coupler.

* * * * *